(12) United States Patent
Koike et al.

(10) Patent No.: US 7,476,738 B2
(45) Date of Patent: Jan. 13, 2009

(54) METHOD FOR IDENTIFYING MOLECULAR WEIGHT OF A PHOSPHORIC ACID MONOESTER COMPOUND AND AN ADDITIVE FOR MASS SPECTROMETRY

(75) Inventors: Tohru Koike, Hiroshima (JP); Norio Minami, Amagasaki (JP); Akihiko Kawasaki, Amagasaki (JP)

(73) Assignee: NARD Institute Ltd. (JP)

( * ) Notice: Subject to any disclaimer, the term of this patent is extended or adjusted under 35 U.S.C. 154(b) by 489 days.

(21) Appl. No.: 10/547,972

(22) PCT Filed: Dec. 24, 2003

(86) PCT No.: PCT/JP03/16512

§ 371 (c)(1),
(2), (4) Date: Sep. 6, 2005

(87) PCT Pub. No.: WO2004/079358

PCT Pub. Date: Sep. 16, 2004

(65) Prior Publication Data

US 2006/0183237 A1   Aug. 17, 2006

(30) Foreign Application Priority Data

Mar. 7, 2003 (JP) .............................. 2003-061939

(51) Int. Cl.
*C07F 3/06* (2006.01)
*G01N 33/48* (2006.01)

(52) U.S. Cl. .............................. 546/2; 436/81; 436/815; 546/22

(58) Field of Classification Search ................... 546/21, 546/2, 27, 22; 436/81, 815
See application file for complete search history.

(56) References Cited

U.S. PATENT DOCUMENTS

| 2002/0076739 A1 | 6/2002 | Aebersold et al. |
| 2004/0198712 A1 | 10/2004 | Koike et al. |
| 2005/0038258 A1 | 2/2005 | Koike et al. |
| 2006/0131239 A1 | 6/2006 | Koike et al. |

FOREIGN PATENT DOCUMENTS

| EP | 1 455 189 A1 | 9/2004 |
| EP | 1 614 706 A1 | 1/2006 |
| WO | WO 00/11208 | 3/2000 |
| WO | WO 03/053932 A1 | 7/2002 |
| WO | WO 2004/078342 A1 | 9/2004 |
| WO | WO 2004/078828 A1 | 9/2004 |

OTHER PUBLICATIONS

"A novel diiron complex as a functional model for hemerythrin"—Hidekazu Arii, et al., Journal of Inorganic Biochemistry 82, pp. 153-162 (2000).
"Dinuclear Cobalt (II) Complexes Containing 1,3-(or 1,5-)Bis[bis-(2-pyridylmethyl)amino]-2-propanolato (or -3-pentanolato): Preparation and Reaction with Molecular Oxygen"—Suzuki et al.—Bull. Chem. Soc. Jpn., 63, 1115-1120 (1990).
"Synthesis, Characterization, and Reversible Oxygenation of u-Alkoxo Diiron (II) Complexes with the Dinucleating Ligand N,N,N',N'—Tetrakis-{(6-methyl-2-pyridyl)methyl{cube root}-1,3-diaminopropan-2-olate"—Suzuki et al.—J. Am. Chem. Soc., vol. 117, No. 45, pp. 11220-11229.
Journal of the Chemical Society, Chem. Commun., 1995—"Preparation and Study of Dinuclear Zinc(II) Complex for the Efficient Hydrolysis of the Phosphodiester Linkage in a Diribonucleotide"—M. Yashiro et al.—pp. 1793 to 1794.
Letters in Peptide Science, vol. 8, No. 1, 2001—"Chemical and functional characterization of metal-binding pseudotripeptides with different functionalized N-alkyl residues"—L. Seyfarth et al.—pp. 13-20.
Rapid Communications in Mass Spectrometry, vol. 17, Issue 18, Aug. 7, 2003—"Matrix-assisted laser desorption/ionization time-of-flight mass spectrometry of phosphorylated compounds using a novel phosphate capture molecule"—H. Takeda et al.—pp. 2075-2081.
1. Trinuclear Zn (II) complex for the efficient and structure dependent hydrolysis of RNA; 2. Zinc (II) complexes of tetrapodal ligands derived from tetra-substituted 1, n-diaminoalcohols; and 3. Enhanced Nucleophilicity and Depressed Electrophilicity of Peroxide by Zinc (II), Aluminum (III) and Lanthanum (III) Ions.

*Primary Examiner*—Charanjit S Aulakh
(74) *Attorney, Agent, or Firm*—Gerald E. Hespos; Anthony J. Casella

(57) ABSTRACT

The present invention provides a method for confirming existence of a phosphoric acid monoester compound (peptide, saccharine and the like) and easily identifying the molecular weight thereof even among biological samples including a plurality of compounds, and an additive for a mass spectrometry used for the method. In the method according to the present invention, a complex compound exhibiting extremely high coordination ability to a phosphoric acid monoester group and configured of single kind of zinc isotopes is used to obtain a plurality of mass spectrum data, and then the data are compared.

8 Claims, 6 Drawing Sheets

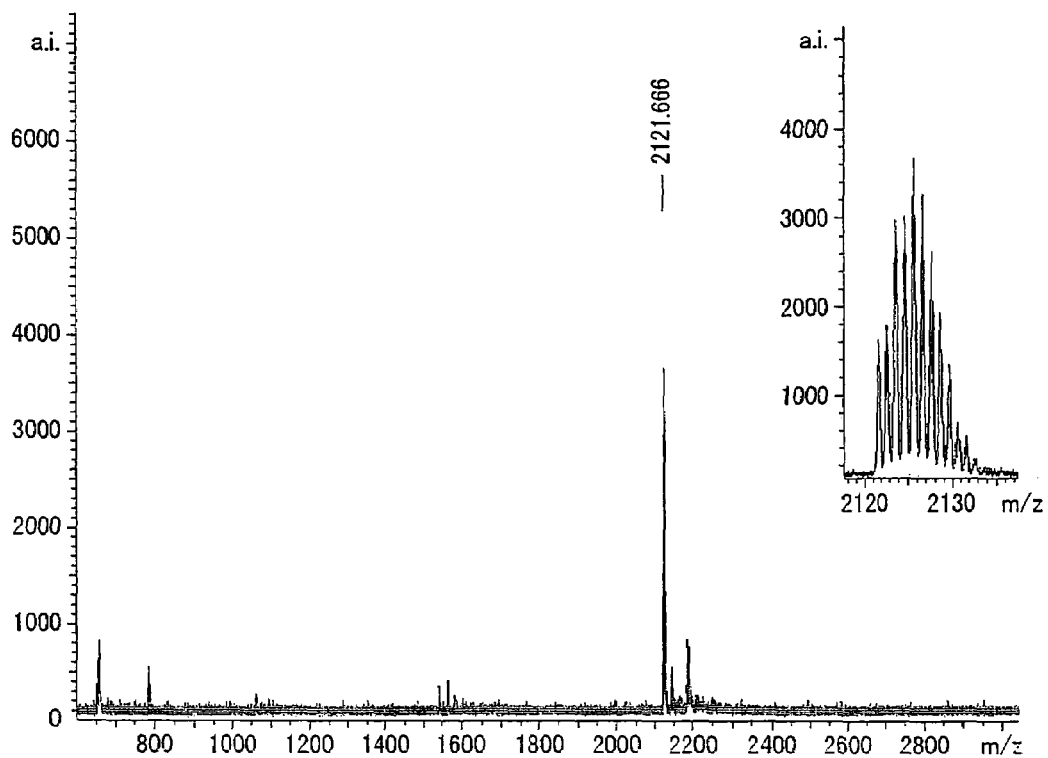
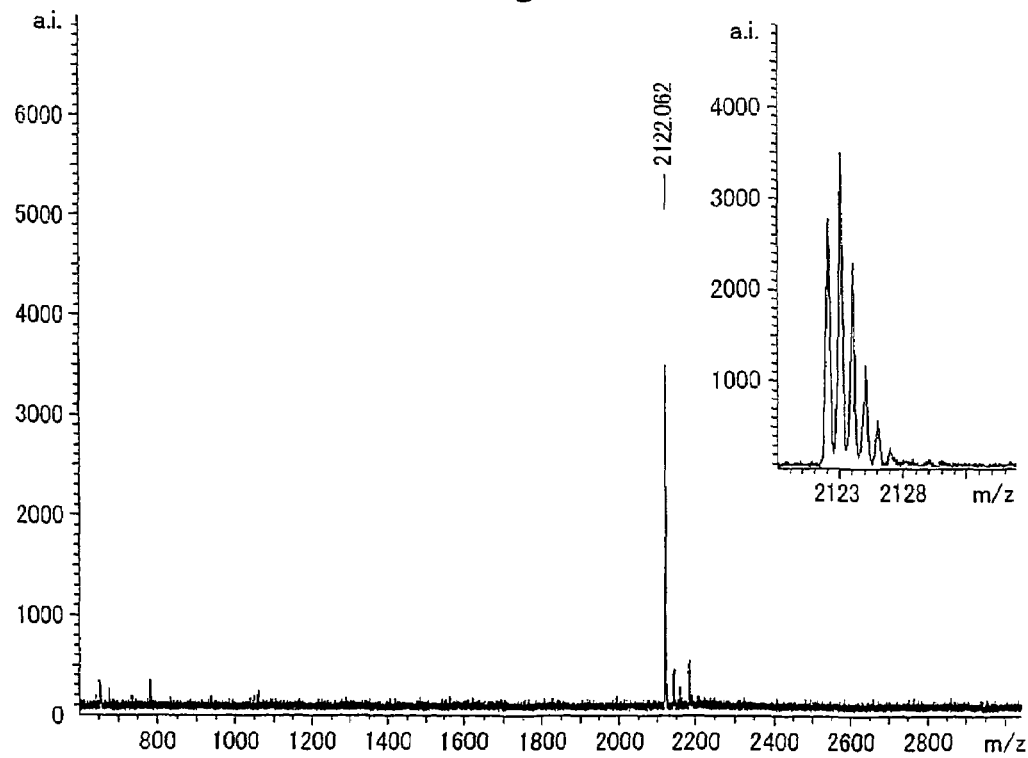

METHOD FOR IDENTIFYING MOLECULAR WEIGHT OF A PHOSPHORIC ACID MONOESTER COMPOUND AND AN ADDITIVE FOR MASS SPECTROMETRY

TECHNICAL FIELD

The present invention relates to a method for identifying a molecular weight of a phosphoric acid monoester compound included in biological sample and the like, and an additive for mass spectrometry used in the method.

BACKGROUND ART

There are known in vivo enzymes having serine, threonine or tyrosine residue at a specific site such as an active center. The enzymatic activity of these enzymes is controlled by phosphorylating, i.e. monoesterification by a phosphate, or dephosphorylating hydroxyl group in these residues by an enzyme called kinase. Also, there are known enzymes whose enzymatic activity is controlled by phosphorylating or dephosphorylating a nitrogen in lysin, arginine or histidine, or a carboxyl group in aspartic acids or glutamic acids.

One of the examples of the metabolic systems which are controlled by the aforementioned phosphorylation-dephosphorylation is a system of suppressing synthesis of glycogen and decomposing the same. This metabolic system is primarily cascade-controlled by the phosphorylation-dephosphorylation.

A recent study has elucidated that the phosphorylation-dephosphorylation plays a significant role in disease-related metabolic systems.

For instance, it is said that one of the causes of cell carcinogenesis is abnormality in the phosphorylation-dephosphorylation. Specifically, progress and stop of cell cycle are controlled by phosphorylation or dephosphorylation of various enzymes, i.e. proteins. Cycline and cycline-dependent kinase (CDK) are relevant factors in the phosphorylation. In case where the mechanism relating to cycline and CDK is impaired, phosphorylation or dephosphorylation may be uncontrollable, thereby abnormal proliferation of cells is triggered.

In addition to the above, facts are known that protein kinase C is related with degranulation of histamine causative of allergic disorders such as atopic dermatitis and pollen allergy, and that phosphorylated tau-protein is causative of neurofibrillary tangle in the brains of Alzheimer's patients.

In view of the above, comprehending which enzymes, i.e. proteins, in biological samples are phosphorylated or dephosphorylated could provide useful measures not only in investigating expression of genes in living tissue cells and evaluating the enzymatic activity of the cells, but also in diagnosing diseases or medical treatment.

The conventional methods for identifying phosphorylated proteins or dephosphorylated proteins have various drawbacks.

For instance, while an enzyme immunoassay is advantageous in analyzing a target protein sample of a very small amount, it is difficult to obtain antibodies of the target protein of a sufficient amount. Further, in case that the level of the target protein is several kDa or lower, it is impossible to prepare an antibody that is securely bonded to a site in the protein where phosphorylation occurs.

There is proposed a method for detecting a protein specifically bonded by a phosphoric acid with use of a phosphoric acid labeled with a radioactive isotope $^{32}P$. However, special attention should be paid in handling radioactive isotopes, and appropriate administration and disposal of waste liquid of the radioactive isotopes are required.

There is proposed an idea of applying two-dimensional electrophoresis in view of the fact that electric charges are differentiated between phosphorylated proteins and dephosphorylated proteins. However, it is extremely difficult to identify the spot of a phosphorylated or dephosphorylated protein in analyzing a sample derived from a living organism, because the sample contains a variety of proteins. Furthermore, use of a radioactive isotope to identify the spot involves the aforementioned problems.

The document, Morio YASHIRO, et al, [Preparation and Study of Dinuclear Zinc (II) Complex for the Efficient Hydrolysis of the Phosphodiester Linkage in a Diribonucleotide], Journal of the Chemical Society, Chemical communications, pp. 1793-1794 (1995), recites a zinc complex. The zinc complex has a function that two zinc ions act on the phosphoric acid group in dinucleotide and dissociate the dinucleotide. However, the function of the zinc complex disclosed in the document is merely a catalyst. The document does not disclose the ability of the zinc complex to bond coordinately to a phosphoric acid group. The experiments conducted by the inventors of the present invention reveal that a dissociation constant of the zinc complex to a phosphoric acid group sandwiched by two nucleotides, namely a phosphoric diester group, is extremely high. In other words, the zinc complex has a low coordinatability to a phosphoric diester moiety.

Further, the document, Hidekazu ARII, et al., [A novel diiron complex as a functional model for hemerythrin], Journal of Inorganic Biochemistry, 82, pp. 153-162 (2000), recites an iron complex having a structure analogous to the structure of the zinc complex. The iron complex, however, is a product synthesized as a model of hemerythrin, namely a carrier protein carrying oxygen molecules. As is the case with the above mentioned document, this document neither discloses nor suggests coordinate bond of the iron complex to a phosphoric monoester moiety at all.

The inventors of the present invention have already developed a method for identifying peptide and the like having a phosphoric acid monoester group. In the method, a complex which specifically bonds coordinately to an anionic substituent such as a phosphoric acid monoester group is used, and mass spectra of samples with and without the aforementioned complex are compared, thereby information on the compound which the phosphoric acid monoester group bonded can be obtained. That is, since values of molecular ion peaks between the compound with the complex and the compound without the complex are different depending on the existence of the complex, the molecular weight of the compound having the phosphoric acid monoester group can be identified.

However, except for pure samples, i.e. purified samples, when a sample including a plurality of compounds is analyzed, a molecular ion peak to be detected may not be identified even if a chart is enlarged. Indication of ion peaks may vary depending on distribution of isotopes of atoms configured of a compound. Therefore, indication of molecular ion peaks is different between the compound with the complex and the compound without the complex, and it may be difficult to identify the peaks.

DISCLOSURE OF THE INVENTION

Under the above mentioned circumsatnce, an object of the present invention is to provide a method for easily identifying a molecular weight of a phosphoric acid monoester compound, i.e. peptide, saccharide and the like, among even the sample including a plurality of compounds such as biological sample.

Another object of the present invention is to provide an additive for mass spectrometry which can be used in the aforementioned method.

In order to solve the above objects, the inventors dedicated themselves to research further on developed metal complexes which exhibit a high binding ability on phosphoric acid monoester groups. They found that a molecular weight of a phosphoric acid monoester compound is easily identified by treating plural complex compounds coordinated by single kind of zinc isotopes on a sample in order to obtain plural mass spectra thereof, and then by comparing these mass spectra. Finally they completed the present invention.

A method for identifying a molecular weight of a phosphoric acid monoester compound, comprising steps of:

(1) mixing a complex compound including a compound (I) having single kind of zinc isotopes and a sample in a solvent to obtain a solution, and then acquiring a mass spectrum of the solution,

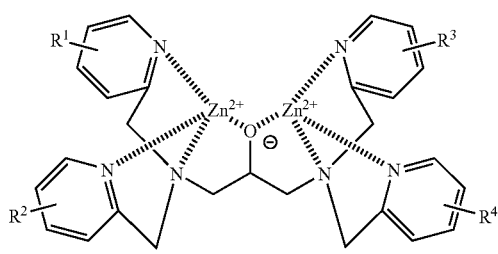

(I)

[wherein $R^1$ to $R^4$ are hydrogen atoms or substituents];

(2) mixing a complex compound including a compound (I) having another kind of zinc isotopes and the sample in a solvent to obtain a solution, and then acquiring a mass spectrum of the solution; and (3) identifying the molecular weight of the phosphoric acid monoester compound by comparing the mass spectra.

In the above method, when a phosphoric acid monoester compound is included in a sample, molecular ion peaks may be observed at different sites between two mass spectra. In case of using compounds (I) having identical basic skeletons except for the zinc isotopes, when both of the molecular ion peaks are compared, the sites of the ion peaks spaced-apart by a value obtained by doubling a difference in the molecular weight between the two used zinc isotopes (when each molecular in the phosphoric acid monoester compounds has a plurality of phosphoric acid monoester groups, the value is obtained by multiplying the number of the group), while both of the peaks have almost identical shapes. Therefore, the molecular ion peaks of the phosphoric acid monoester compounds can be identified easily, and at the same time, the molecular weight thereof can be identified.

As the complex compound (I), all of the $R^1$ to $R^4$ are preferably hydrogen atoms. Since the structure of such compound (I) has the simplest, the compound is easily produced, and the molecular ion peaks are more simplified.

Further, an additive for mass spectrometry according to the present invention is used for identifying a molecular weight of a phosphoric acid monoester compound, comprising: a reagent having a complex compound including a compound (I) having single kind of zinc isotopes, and a reagent having a complex compound including a compound (I) having another kind of zinc isotopes;

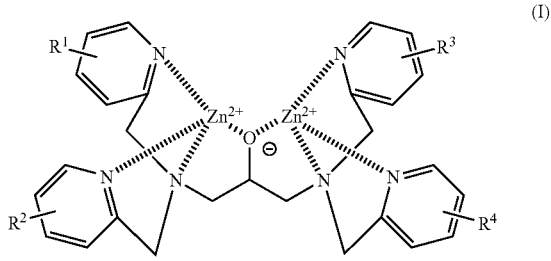

(I)

[wherein $R^1$ to $R^4$ are hydrogen atoms or substituents].

As the complex compound, all of the $R^1$ to $R^4$ are preferably hydrogen atoms. Because the structure of the complex compound is the simplest, and such a compound is easily produced.

As the complex compound, it is preferable that the compound (I) further forms a complex with an acetate ion. The compound is more stable and easier for preservation than that is not coordinated to an acetate ion. In addition, when the complex compound is added into a sample, a phosphoric acid monoester group can be coordinated to the complex compound by interchanging place with the acetate ion, therefore, a phosphoric acid monoester compound can be detected as well as in the case when the compound which is not coordinated to an acetate ion is used.

The reagent is preferably in a state of a salt, because it has excellent stability in preservation. The reagent is also preferably in a state of a solution, because it can be used as a sample for mass spectrometry by being added into a sample solution or by adding a sample into the additive solution.

BRIEF DESCRIPTION OF THE DRAWINGS

FIG. 3 is amass spectrum of a composite material of a sample and a natural zinc isotope complex; because of existence of a plurality of zinc isotopes, peaks are complicated;

FIG. 4 is amass spectrum of a composite material of a sample and $^{64}$Zn zinc complex. Since the zinc included in the complex is single kind of isotopes, peaks are simpler than that of the natural zinc isotope complex.

BEST MODE FOR CARRYING OUT THE INVENTION

Figure 1:
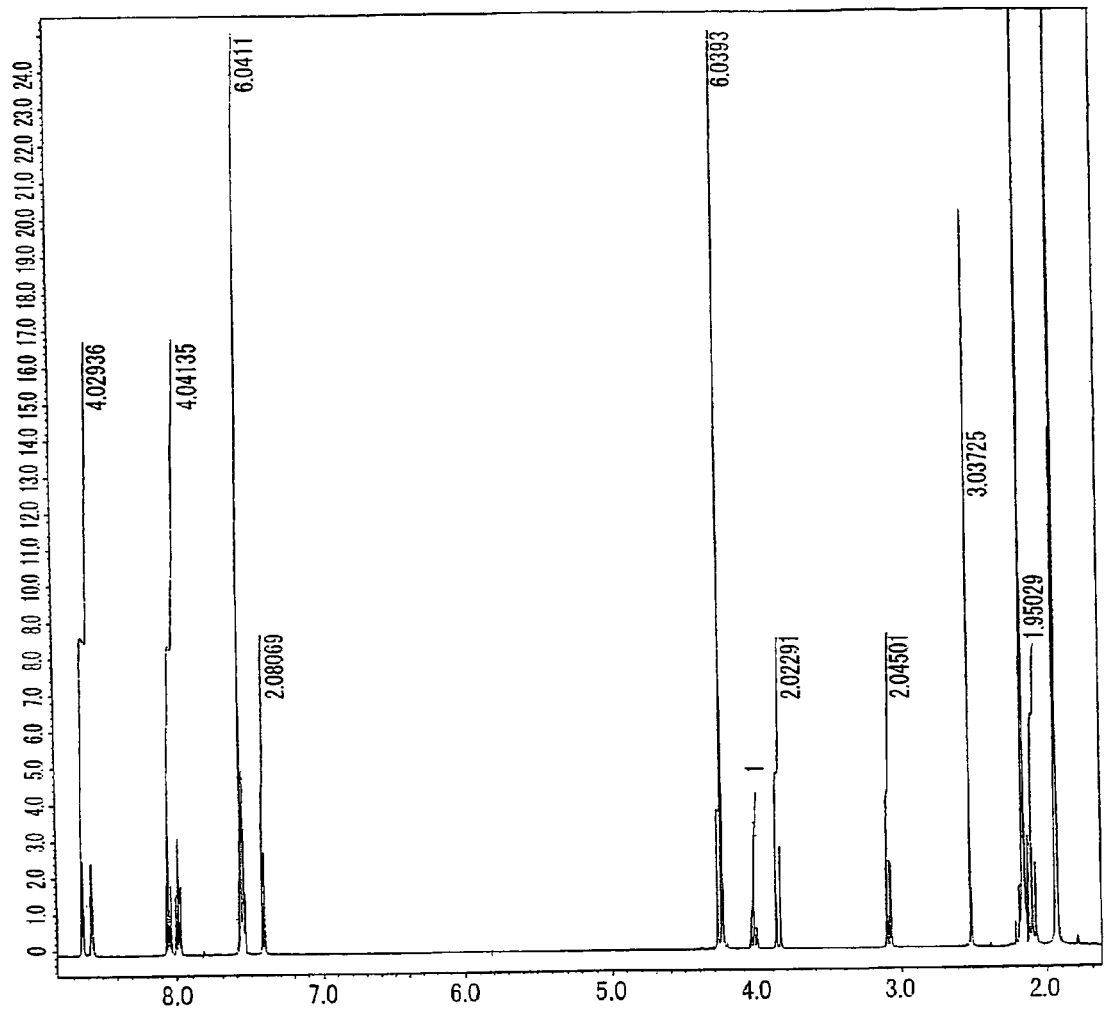
FIG. 1 shows a result of $^1$H NMR on a complex compound according to the present invention.

A primary feature of the method according to the present invention is that with a use of two complex compounds including zinc isotopes each having different molecular weights, mass spectra of each sample coordinated to respective complex compounds are compared, accordingly existence of a phosphoric acid monoester compound included in a sample can be easily confirmed, and a molecular weight thereof can be identified.

There have been known various metal complexes capable of being bonded to a phosphoric acid group. However, it has not been recognized that a complex compound according to the present invention has a high binding ability to a phosphoric acid monoester group. In addition, the inventors of the present invention have developed an invention, in which a complex compound according to the present invention is used as an additive for mass spectrometry (an additive for analysis by mass spectrometry). The present invention is made by improving the aforementioned invention, and provides easier confirmation of a phosphoric acid monoester compound and identification of a molecular weight thereof.

Hereinafter, embodiments of the present invention and advantages thereof will be explained.

In a method according to the present invention, primarily, (1) a complex compound including a compound (I) having single kind of zinc isotopes is mixed with a sample in a solvent to obtain a solution, and then a mass spectrum of the solution is acquired.

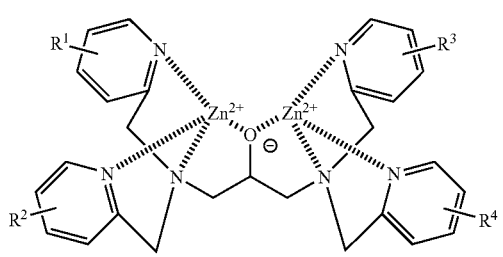

[wherein $R^1$ to $R^4$ are hydrogen atoms or substituents].

First, the complex compound including the compound (I) having single kind of zinc isotopes will be explained hereinafter.

In the compound (I), substituents in the definition of $R^1$ to $R^4$ are not specifically limited, as far as the substituents do not disturb coordination of the compound (I) to a phosphoric acid monoester group. Examples of the substituents are: a straight chain or a branched chain C1-C6 alkyl group, an amino group, a hydroxy group, a carbamoyl group, a straight chain or a branched chain C1-C6 alkoxy group, a halogen atom, a nitro group, a sulfonic acid group, a carboxyl group, a formyl group, an acyl group, a cyano group, an aminomethyl group, a hydroxymethyl group, and the like.

As the $R^1$ to $R^4$, it is preferable that they are hydrogen atoms. A compound of which $R^1$ to $R^4$ are hydrogen atoms can be easily produced with low cost, and molecular ion peaks to be obtained may be simpler. Further, as the $R^1$ to $R^4$, it is preferable that they are electron donating substituent groups at the 4 or 6 position on the pyridine ring. The compound is electrically enriched with pyridine nitrogen by the electron donating substituent group that has been introduced to an appropriate position. Accordingly, the compound is highly coordinated to zinc, thereby making it possible to produce the compound easily. Such a compound is stable.

The $R^1$ to $R^4$ may be identical to or different from each other. However, they are preferably identical to each other, mainly because synthesizing such a compound is easy.

In the formula (I), zinc is selected as coordinate metal because zinc is highly coordinated to a phosphoric acid monoester group.

A complex compound including a compound (I) means that an essential part in the complex compound is the compound (I). For example, for a purpose of further stabilization of the compound (I), an acetate ion and the like may be coordinated to the compound (I) as shown in the following formula.

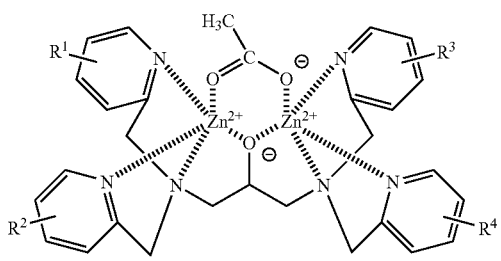

The compound (I) exhibits extremely high coordination ability to a phosphoric acid monoester group. Accordingly, when a compound having a phosphoric acid monoester group exists in a solution, an interchange is promptly occurred even if other compounds are coordinated to the compound (I), thereby a composite material of the complex compound and the phosphoric acid monoester compound is formed.

Natural zinc isotope has molecular weight of 64, 66, 67, 68 or 70. A complex compound configured of single kind of isotopes selected from any one of the above is used in Process (1).

In Process (1), the complex compound and a sample are mixed in a solvent to obtain a solution. Then, because the compound (I) exhibits an extremely high coordination ability to a phosphoric acid monoester group, the compound (I) promptly coordinates to a phosphoric acid monoester compound in the sample to form a composite material. Accordingly, it is not particularly necessary to heat the mixed solution or to spend time to form a composite material. However, as a matter of course the solution may be treated, as long as it is within a range of the purpose of the present invention. For example, the solution may be heated.

Furthermore, in order to mix the complex compound and a sample in the solvent, the complex compound and a sample may be added into a solvent, or a sample or a solution thereof may be added into the complex compound solution, or the complex compound or a solution thereof may be added into a sample solution.

A solvent used in this process is not particularly limited as long as a solvent can dissolve the complex compound of the present invention and a sample in a range that the present invention can exert an effect. Examples of the solvents are: water (including a buffer or a solution containing a salt other than a buffer); alcohols such as methanol and ethanol; acetonitrile; amide such as dimethylformamide and dimethylacetamide; and mixed solutions thereof. Among them, water or a mixed solution made of water and a water-soluble organic solvent (an aqueous solvent) are preferable, because they are excellent in dissolving the complex compound of the present invention, biological samples, and the like.

When the complex compound and a sample are mixed in a solvent to obtain a solution in Process (1), it is not necessary to dissolve the complex compound and a sample completely. However, it is preferable that they are dissolved enough for the complex compound to be capable of coordinating to a phosphoric acid monoester compound in a sample. That is, the solution does not have to be a complete solution, and undissolved elements can remain in some parts.

Subsequently, the solution (a mixed solution) including a composite material of the complex compound of the present invention and a phosphoric acid monoester compound is analyzed by mass spectrometry. In a mass spectrometry, the mass spectrometer which is suitable for a detection of compound to be detected may be used. Since the purpose of the present invention is mainly to obtain a molecular weight of a polymer molecule included in biological samples, MALDI TOF-MAS (Matrix Assisted Laser Desorption Ionization-Time of Flight Mass Spectrometer) is preferably used, because of its ability to measure even giant molecules such as protein.

The purpose of the present invention is mainly to identify a molecular weight of phosphate monoesterified peptide. However, a sample is not limited to the above, and for example, a composite material of phosphorylated peptide and saccharide, and phosphorylated saccharide may be applied to.

Then, Process (2) is carried out in a same manner as Process (1). Particularly, a compound (I) in Process (2) is preferably same as that in Process (1). Because shapes of molecular ion peak to be compared result in almost identical to each other, and identification of the molecular ion peaks will be simplified. In Process (2), it is essential to use a complex compound configured of a kind of zinc isotopes different from that used in Process (1). If same kind of isotopes are used in Process (1) and (2), an effect of the present invention can not be exerted.

Furthermore, the above-mentioned Process (1) and (2) may be carried out at the same time. That is, an embodiment wherein an additive for mass spectrometry including two kinds of compounds (I) configured of zinc isotopes having different molecular weights each other is added to a sample and the mixture is analyzed by mass spectrometry is in the scope of the present invention. However, it is difficult to identify a molecular ion peak of a complex of a phosphoric acid monoester compound and the compound (I), when a sample has a variety of compounds. Therefore, an embodiment in which Process (1) is carried out first and then Process (2) follows is preferable.

Subsequently, in Process (3), a molecular weight of a phosphoric acid monoester compound is identified by comparing the mass spectra obtained in Process (1) and (2).

First of all, the mass spectra are compared in order to find different peaks. The molecular ion peaks of the compound (I) or the complex compound configured of different kinds of zinc isotopes are naturally different. When a phosphoric acid monoester compound is included in a sample, since the compound (I) coordinates to a phosphoric acid monoester compound at an almost quantitatively to form a composite material, values of the molecular ion peaks of the composite material are different depending on the different value in molecular weights of the zinc isotopes.

It is easy to identify the molecular ion peak of the composite material by the mass spectra obtained in the aforementioned Process (1) and (2). The shapes of the both molecular ion peaks are almost identical, therefore, by enlarging the both peaks to compare, it is easy to judge whether the both molecular ion peaks result from the same kind of phosphoric acid monoester compounds or not. In addition, when the same compound (I) is used in the aforementioned Process (1) and (2), the difference in the molecular weight of the both peaks are equal to a value obtained by integral multiple of the doubled difference in the molecular weight of the zinc isotopes. Therefore, the both molecular ion peaks are easily identified. This is because two zinc atoms are coordinated to the complex compound used in the present invention, and also because the complex compound of the present invention coordinates almost quantitatively to a phosphoric acid monoester group existing in a sample. Therefore, the difference in the both molecular weights can be anticipated to some extent.

For example, when the same compound is used as a compound (I), and when $^{64}Zn$ and $^{68}Zn$ are used as zinc isotopes, a difference in a molecular weight of composite materials of phosphorylated peptide and the complex compounds according to Process (1) and (2) is an integral multiple of 8 (a value obtained by multiplying 8 with the number of phosphoric acid monoester group existing in one molecular in the compound). In addition, from the measured difference in the molecular weight, the number of a phosphoric acid monoester group existing in one molecular in a phosphoric acid monoester compound can be identified.

Further, since single kind of zinc isotopes are used in the present invention, a complexity of molecular ion peaks derived from the use of plurality kinds of zinc isotopes may be reduced. Splitting of molecular ion peaks is caused only by carbon isotopes and the like, which is another reason for easier identification of the molecular ion peaks.

Next, subtracting a molecular weight of the compound (I) from a molecular weight obtained by the identified molecular ion peaks enables to identify a molecular weight of a phosphoric acid monoester compound. For example, in case of using a compound shown below as a compound (I) (wherein all $R^1$ to $R^4$ are hydrogen atoms, and ion isotope is $^{64}Zn$), when the number of a phosphoric acid monoester group binding to a phosphoric acid monoester compound is one, a molecular weight of a phosphoric acid monoester compound can be identified by subtracting 579 from a value of a molecular ion peak of a composite material. The reason why not subtracting 581, which is a molecular weight of the compound (I) shown below, is because two hydrogen positive ions are considered to be eliminated from the phosphoric acid monoester group when a phosphoric acid monoester compound coordinates to the compound (I), therefore the atomic weight thereof needs to be added.

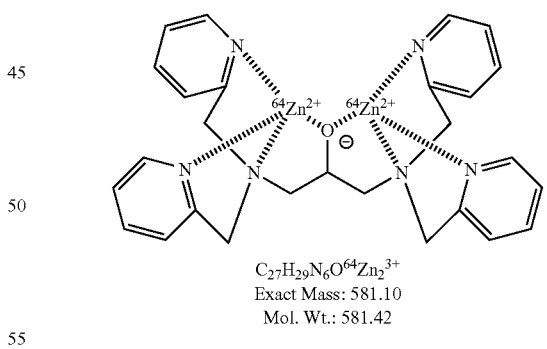

$C_{27}H_{29}N_6O^{64}Zn_2^{3+}$
Exact Mass: 581.10
Mol. Wt.: 581.42

An additive for a mass spectrometry according to the present invention is used for identifying a molecular weight of a phosphoric acid monoester compound, and comprises a reagent having a complex compound including a compound (I) having single kind of zinc isotopes, and a reagent having a complex compound including a compound (I) having another kind of zinc isotopes.

A complex compound including a compound (I) having single kind of zinc isotopes and a complex compound including a compound (I) having another kind of zinc isotopes mean same as the above.

A reagent having a complex compound means that the reagent may be in a state of a salt or a solvate, i.e. hydrates and the like, of the complex compound. A counter ion consisting of a salt is not limited as long as it does not disturb effects of the present invention, and it is preferable to use the counter ion which allows a reagent having a complex compound to form a crystal, and which improves a stability of the complex compound. For example, a perchlorate ion ($ClO_4^-$) is preferable. In addition, forms of a certain hydrate may give an improvement in the stability against moisture and the like.

Furthermore, an additive for mass spectrometry according to the present invention may be in a state of a solution. When the additive is in the state of solution, it is convenient since it may be added into a sample solution, and a sample or a solution thereof may be added into the solution directly. As a solvent used for the solution, the above mentioned solvent to mix a complex compound and a sample may be used. Further, an additive for improving a stability of the complex compound may be added.

Including a reagent means that two kinds of reagents may be included in a composition. However, as described in the above, Process (1) and Process (2) are preferably carried out one by one, even though they may be carried out simultaneously. Accordingly, an additive for mass spectrometry according to the present invention is preferably in a kit having each reagent separately.

The compound (I) may be produced easily according to Scheme 1.

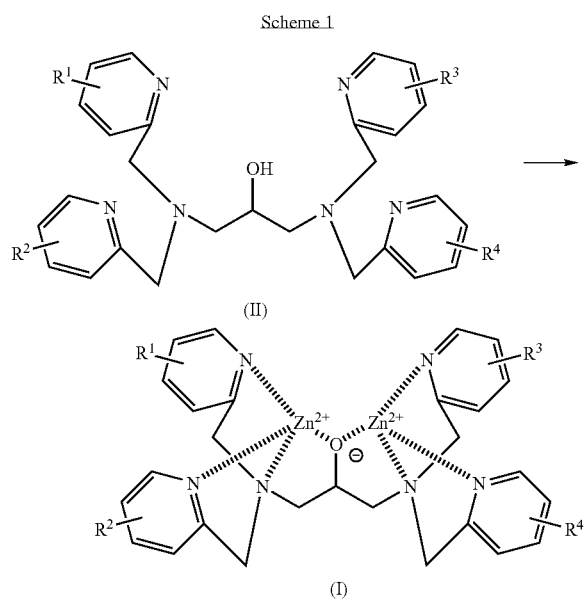

[wherein $R^1$ to $R^4$ are hydrogen atoms or substituents].

In the above Scheme 1, a compound (II) is reacted with a single kind of zinc isotope compound to synthesize the compound (I). The compound (II) which is a raw material compound can be synthesized in the following Scheme 2. As the single kind of zinc isotope compound, zinc metal, zinc oxide, zinc salt and the like may be used. The compound (II) can be a salt.

In the above Scheme 1, zinc is easily coordinated to the compound (II) by heating an aqueous solution which is adjusted to be neutral. However, since a zinc compound needs to be dissolved sufficiently, a particle of the zinc had better be atomized by, for instance, having an ultrasonic treatment in advance or being dissolved in hydrochloric acid once. The definition of neutral herein does not mean completely neutral but almost neutral, preferably the pH of the aqueous solvent is adjusted to not less than 6.8.

The aqueous solvent used in Scheme 1 is not limited as long as it is capable of dissolving the compound (II) and a zinc compound. The aqueous solvent may be pure water, distillated water, tap water, buffer solution, or a mixture prepared by adding alcohol, amide or acetonitrile and the like to the above.

A heating temperature is preferably in a range of 30 to 90° C., and more preferably 50 to 90° C. A reaction period may be 10 minutes to a few hours. After the reaction, excessive reagents are removed by such as filtration. Then, the target compound is obtained by cooling the solution slowly and separating precipitated crystals by filtration, or by a common method of recrystallization. The complex compound may be stabilized by being coordinated with such as acetate ion.

The compound (II) may be produced according to Scheme 2.

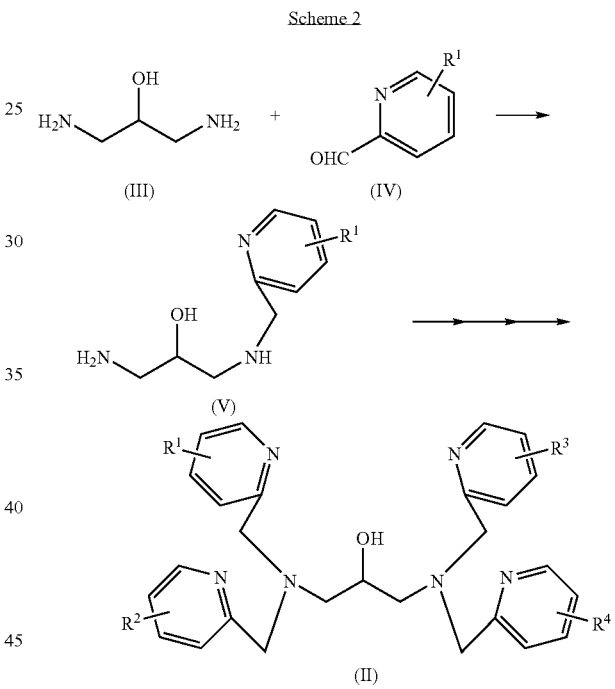

[wherein $R^1$ to $R^4$ are hydrogen atoms or substituents].

Scheme 2 shows a reaction pathway in which 2-pyridylmethyl group having $R^1$ to $R^4$ is added sequentially into a compound (III), i.e. 1,3-diamino-2-propanol which is a raw material compound. The compound (III) used in Scheme 2 may be commercially available. Since the compound (IV) and 2-formylpyridine compound have relatively simple structures, they may be commercially available, or can be synthesized by a well-known method for a person skilled in the art. When the substituents, i.e. $R^1$ to $R^4$ are reactive groups, the substituents may be protected by common protective groups, and the protective groups may be removed appropriately.

In Scheme 2, first, the compound (III) and the compound (IV) are reacted with each other for condensation to yield the compound (V), and then, the 2-pyridylmethyl group is introduced sequentially to synthesize the compound (II). When $R^1$ to $R^4$ are same kind of groups, the compound (II) can be obtained by a single step by using 4 or more equivalents of the 2-formylpyridine compound (IV).

In Scheme 2, reductive amination is carried out as a condensation reaction. A solvent used in the reductive amination is not specifically limited, as long as the solvent is capable of substantially dissolving the compound (III) and the 2-formylpyridine compound such as the compound (IV), and does not inhibit the amination. For instance, alcohols such as methanol, ethanol and isopropanol; ethers such as diethyl ether, tetrahydrofuran and dioxane; water; or a mixed solvent containing two or more of these components can be used as the solvent.

The reductive amination can be carried out with use of a conventional reducing reagent after condensing the compound (III) and the 2-formylpyridine compound, and hydrochloric acids and the like may be added as a catalyst during the condensation. A hydrochloride salt may be used as the compound (III).

An optimal condition regarding the reaction temperature and the reaction time can be optionally selected depending on a kind of a raw material compound or other factors. For example, the reaction may be carried out at a reaction temperature from 20 to 80° C. for a reaction time from 12 to 100 hours.

After the reaction is completed, the solvent and the like are distilled off under depressurization. Then water is added, and the resultant mixture is extracted with a water-insoluble solvent, and an oil phase is dried over anhydrous magnesium sulfate or the like. Thereafter, the solvent is distilled off under depressurization. Subsequently, the residue is purified by a well known process such as silica gel column chromatography, and reactions are carried out by introducing pyridylmethyl, thereby to yield the compound (II).

A method to obtain the compound (II) is not limited to the method as shown in Scheme 2. For example, the compound (II) may be synthesized by the compound (III) and a halogen compound. A method for synthesizing the compound (II) in which all of $R^1$ to $R^4$ are hydrogen atoms is described in the document, M. Suzuki et al., Bull. Chem. Soc. Jpn., Vol. 63, pp1115-1120 (1990), and a method for synthesizing such as the compound (II) in which all of $R^1$ to $R^4$ are methyl group introduced in the 6 position (2 position) is described in the document, Y. Hayashi, et al., J. Am. Chem. Soc., Vol. 117, pp11220-11229 (1995).

Hereinafter, the present invention will be illustrated in more detail with reference to Production Examples and Test Examples, but not limited thereto.

EXAMPLES

Production Example 1-1

Zinc Complex (Salt) According to the Present Invention

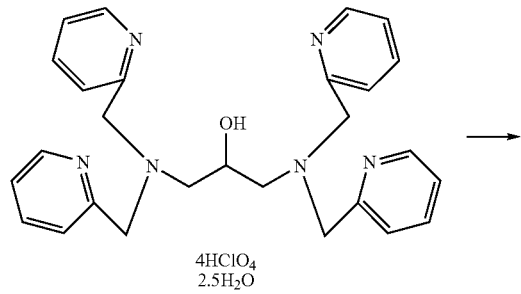

4HClO$_4$
2.5H$_2$O

-continued

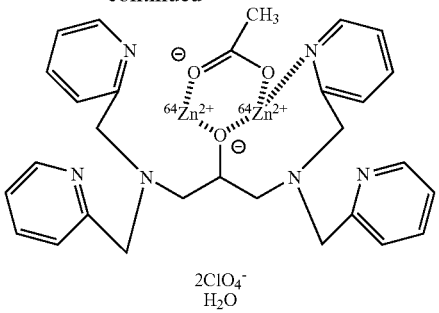

2ClO$_4^-$
H$_2$O

Figure 2:
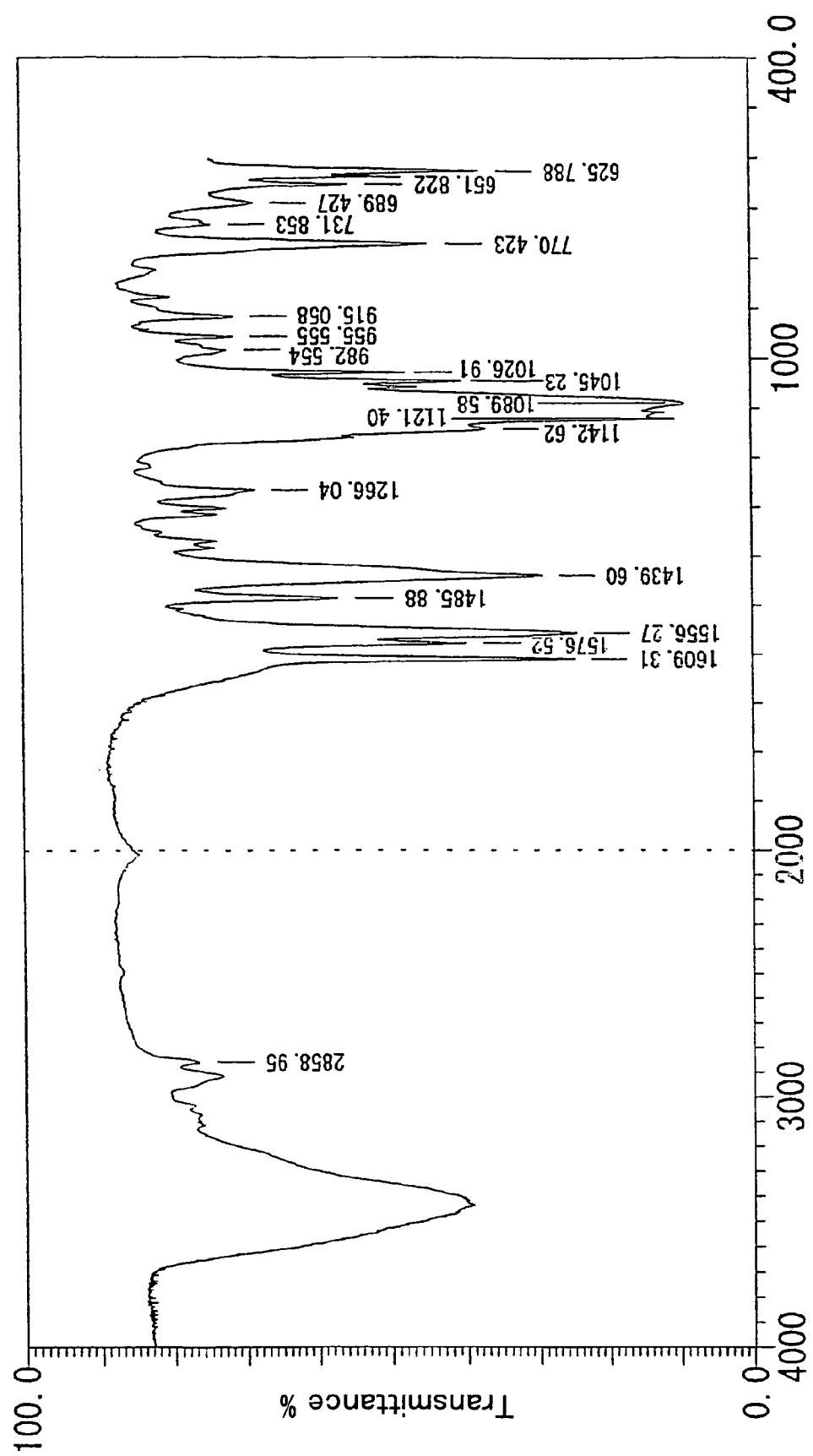
FIG. 2 shows a result of IR on a complex compound according to the present invention.

To 65 mL of water, 902 mg (1 mmoL) of N,N,N',N'-tetrakis[(2-pyridyl)methyl]-1,3-diamino-2-hydroxy propane (hereinafter, it is referred to as "TPAHP") 4-perchlorate 2.5-hydrate and 160 mg (2 mmoL) of $^{64}$ZnO were added. The mixture was sonicated at 50° C. to be dissolved while $^{64}$ZnO was being dispersed. To the solution, 1.0 mL of 1.0M aqueous solution of sodium hydroxide was added, and the solution was filtered after heated for 30 minutes in a water bath at 80° C. Further, 2.0 mL of 1.0M sodium acetate aqueous solution was added dropwise into the stirring solution while the solution was heated in a water bath at 80° C. After the reaction mixture was slowly cooled at a room temperature, the precipitated colorless crystal was filtered by a glass filter, and dried at 50° C. and about 10 mmHg for 3 hours to yield 760 mg (89%) of the target compound. $^1$HNMR and IR spectra of the target compound were acquired. The results thereof are shown in FIGS. 1 and 2 respectively.

Production Example 1-2

Zinc Complex (Salt) According to the Present Invention

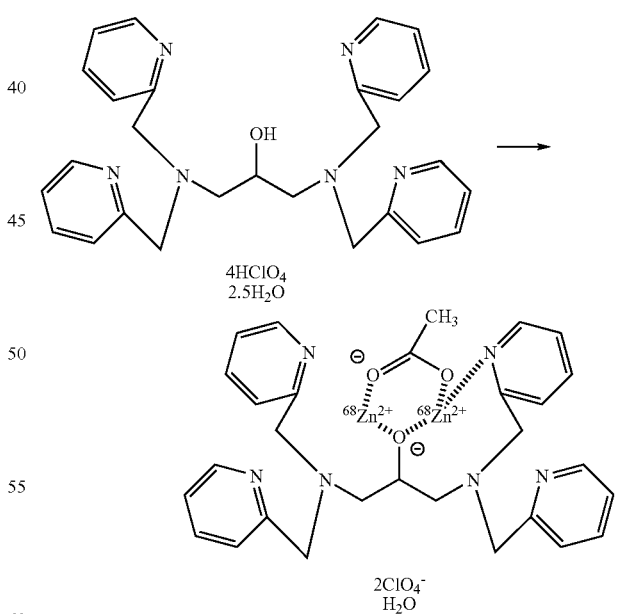

4HClO$_4$
2.5H$_2$O

2ClO$_4^-$
H$_2$O

To 10 mL of water, 658 mg (0.73 mmoL) of TPAHP 4-perchlorate 2,5-hydrate and 100 mg (1.47 mmoL) of $^{68}$Zn were added. The mixture was sonicated at 50° C. to be dissolved while $^{68}$Zn was being dispersed. The $^{68}$Zn had a pretreatment in which $^{68}$Zn had been dissolved in 5 mL of conc. hydrochloric acid in advance, and water therein was distilled off under depressurization, and then $^{68}$Zn was further dried under depressurization by a methanol azeotrope. To the solution, 36.5 mL of 0.1M aqueous solution of sodium hydroxide was added, and the solution was filtered after heated for 30 minutes in a water bath at 80° C. Further, sodium acetate aqueous solution (which was prepared by dissolving 160 mg of sodium acetate in 5 mL of distilled water) was added dropwise into the stirring solution while the solution was heated in a water bath at 80° C. After the reaction mixture was cooled slowly at a room temperature, the precipitated colorless crystal was filtered by a glass filter, and dried at 50° C. and about 10 mmHg for 3 hours to yield 440 mg (70%) of a target compound.

Production Example 1-3

Zinc Complex (Salt) Constituting of Natural Zinc Isotope

To TPAHP (4.39 mmoL) ethanol solution (100 mL), 10M aqueous solution of sodium hydroxide (1.0 eq) was added, and subsequently, zinc acetate (9.66 mmol, 2.2 eq) was added. The solvent was distilled off under depressurization to obtain a brown oil-like residue. The residue was dissolved by adding 10 mL of water. Then, while the residue was being heated, 1.0M sodium perchlorate solution (3.0 eq) was added dropwise into therein to obtain a precipitated creamy-white crystal. The crystal was filtered and dried by heating to yield 2.99 g (79%) of the target compound which was slightly brownish-yellow powder. It was confirmed by $^1$H-NMR (400 MHz), $^{13}$C-NMR (100 MHz) and IR that the obtained result was the target compound.

$^1$H-NMR (DMSO-D$_6$, 400 MHz): δ 2.04(2H, dd, J=12.1 and 12.4 Hz, HC-1,3), 2.53(3H, s, HC-35), 3.06(2H, dd, J=12.1 and 12.3 Hz, HC-1,3), 3.74(1H, t, J=10.4 Hz, HC-2), 4.02-4.34(82H, m, HC-5,13,20,27), 7.54-7.65(8H, m, HC-10,11,18,19,25,26,32,33), 8.06-8.12(4H, m, HC-9,17,24,31), 8.58(4H, dd, J=16.3 and 16.5 Hz, HC-8,16,23,30)
$^{13}$C-NMR (DMSO-D$_6$, 100 MHz): δ 58.0, 60.1, 62.0, 64.6, 122.7, 124.3, 124.4, 139.9, 140.4, 147.0, 147.2, 154.7, 155.1
IR (cm$^{-1}$): ν$_{as}$ (COO) 1556, ν$_3$ (ClO$_4$) 1090

Test Example 1

The each zinc complex compound (each having $^{64}$Zn, $^{68}$Zn and natural isotope Zn as a constituent component) produced in the aforementioned Production Examples 1-1 to 1-3 was dissolved in distilled water to obtain 1 mM aqueous solution. As a sample, phosphorylated P60c-src peptide 521-533 1 mM aqueous solution was used. The following formula shows the structure of the phosphorylated peptide.

To each 5 μL of 1 mM zinc complex aqueous solution, 10 μL of the sample, 30 μL of a buffer solution and 5 μL of distilled water were added to give a total amount of 50 μL of the sample for analysis, and a mass spectrum (MALDI TOF-MAS) of the samples were acquired. Onto a sample plate, 0.5 μL of the sample for analysis was applied, and 0.5 μL of a matrix was promptly added on the sample. The sample and the matrix were mixed by a pipette with a caution that the tip of the pipette should not touch the plate. Afterwards, the sample and the matrix were air-dried for approximately five minutes, and acquired mass spectra. The conditions of the mass spectrometry are as shown below.

MALDI TOF-MAS: autoflex (Brucker Daltonics Inc.)

Matrix: THAP (2,4,6-trihydroxyacetophenone) 40 mg/mL (in acetonitryl)

Buffer solution (for dissolving samples): 10 mM Tris-borate buffer (pH=8.0)

Figure 5:
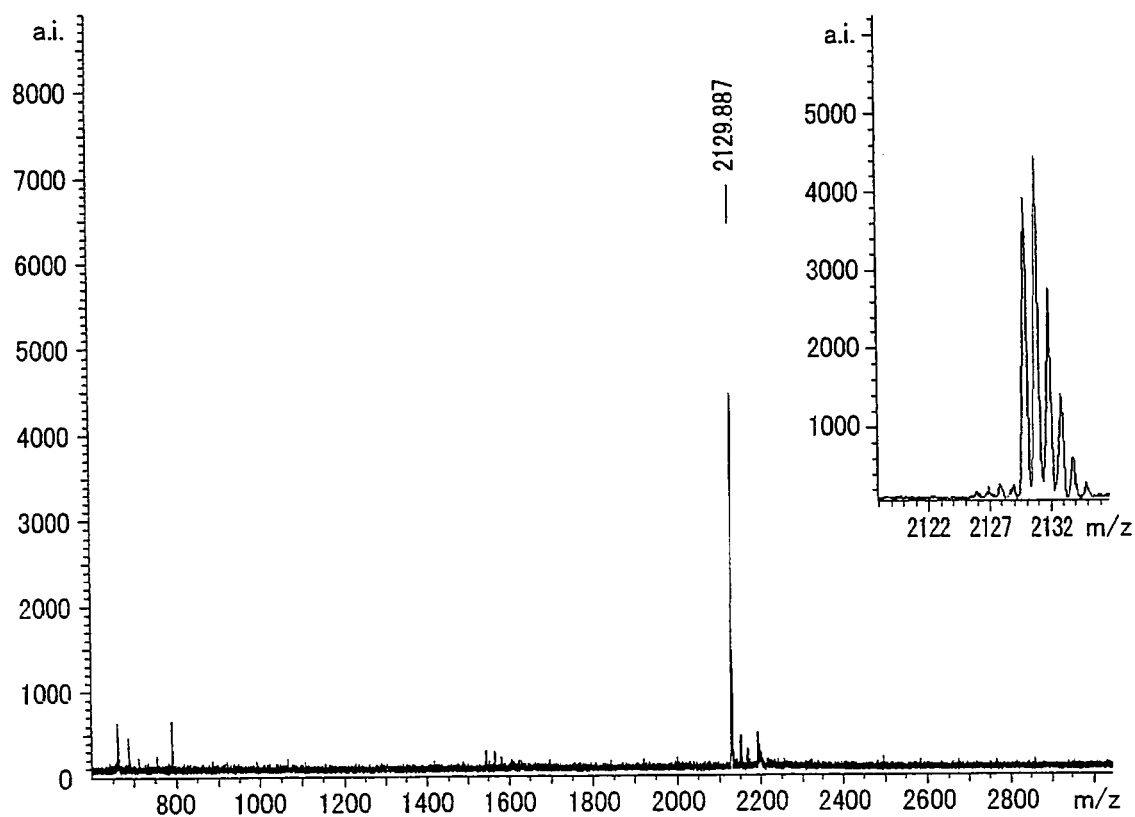
FIG. 5 is amass spectrum of a composite material of a sample and $^{68}$Zn zinc complex; as well as FIG. 4, peaks are simpler than that of the natural zinc isotope complex.

FIG. 3, FIG. 4 and FIG. 5 show the results of the mass spectrometry on the composite materials of the compound and zinc isotopes selected from the natural zinc isotope, $^{64}$Zn zinc isotope or $^{68}$Zn zinc isotope, respectively.

According to the above results, a molecular ion peak of the composite material including $^{64}$Zn zinc was 2122, and that of the composite material including $^{68}$Zn zinc was 2130. Therefore, it is clear that the sample was monophosphate-esterified, and the number of the bonded phosphate group was one. The value subtracted the molecular weight (581) of the complex compound from the molecular weight of the composite compound including $^{64}$Zn zinc was 1541. The value is different from that shown in the above structural formula, because it is considered that the complex compound coordinated to an ionized (i.e. a hydrogen positive ion was eliminated) phosphoric acid monoester compound in peptide as shown in the following formula. That is, adding a molecular weight of the detached hydrogen positive ion, 2, to the obtained molecular weight gives 1543, which accords with the molecular weight according to the data.

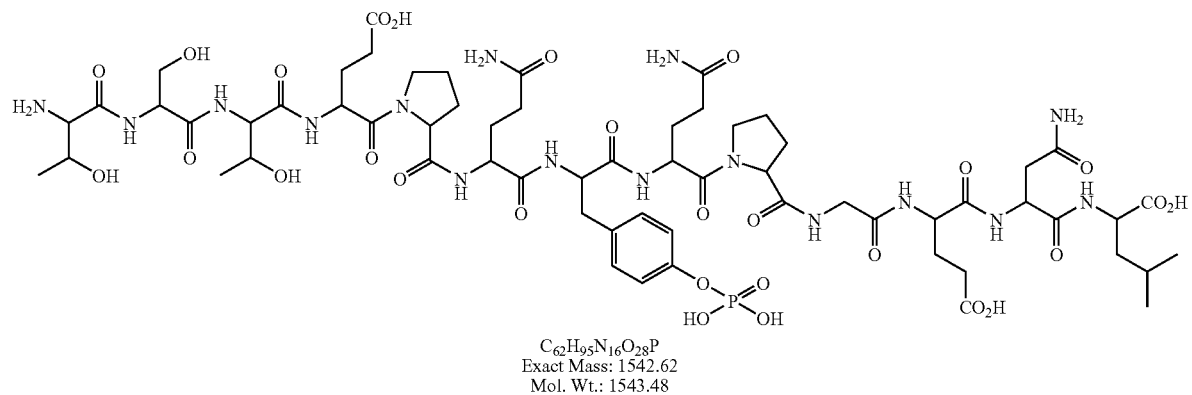

C$_{62}$H$_{95}$N$_{16}$O$_{28}$P
Exact Mass: 1542.62
Mol. Wt.: 1543.48

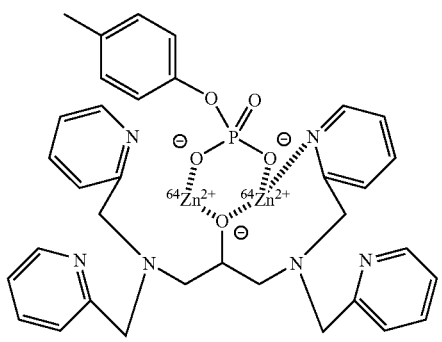

The molecular ion peak of the composite material including the natural zinc isotope is complicated due to existence of a plural kinds of zinc isotopes. On the other hand, the peak is simplified and appears in almost identical shapes when single kind of zinc isotopes are used. Therefore, the present invention demonstrated that a molecular ion peak is easily identified even when a mixed sample such as biological sample is used.

Test Example 2

Using the zinc complexes produced in the aforementioned Production Examples 1-1 and 1-2 (each having $^{64}$Zn and $^{68}$Zn as constituent components), the same method as Test Example 1 was repeated to acquire a mass spectrum thereof. As a sample, phosphorylated P60c-src peptide Substrate II having the following structure was used. As a measuring device, Voyager RP type (PE Biosystem Inc.) was used.

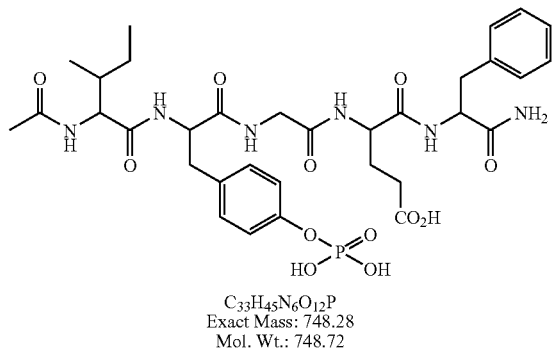

$C_{33}H_{45}N_6O_{12}P$
Exact Mass: 748.28
Mol. Wt.: 748.72

Figure 6:
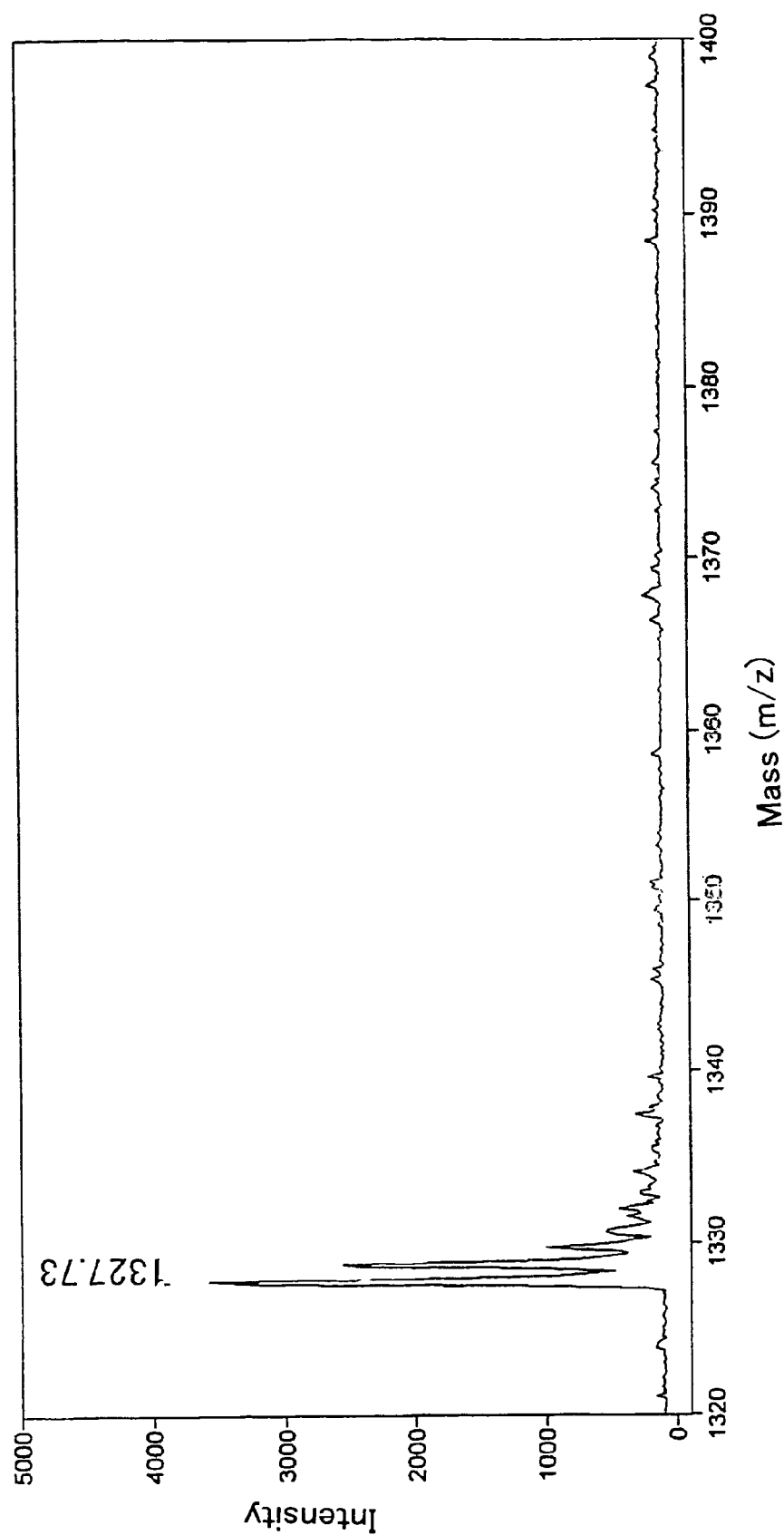
FIG. 6 is a mass spectrum of a composite material of a sample and $^{64}$Zn zinc complex.
Figure 7:
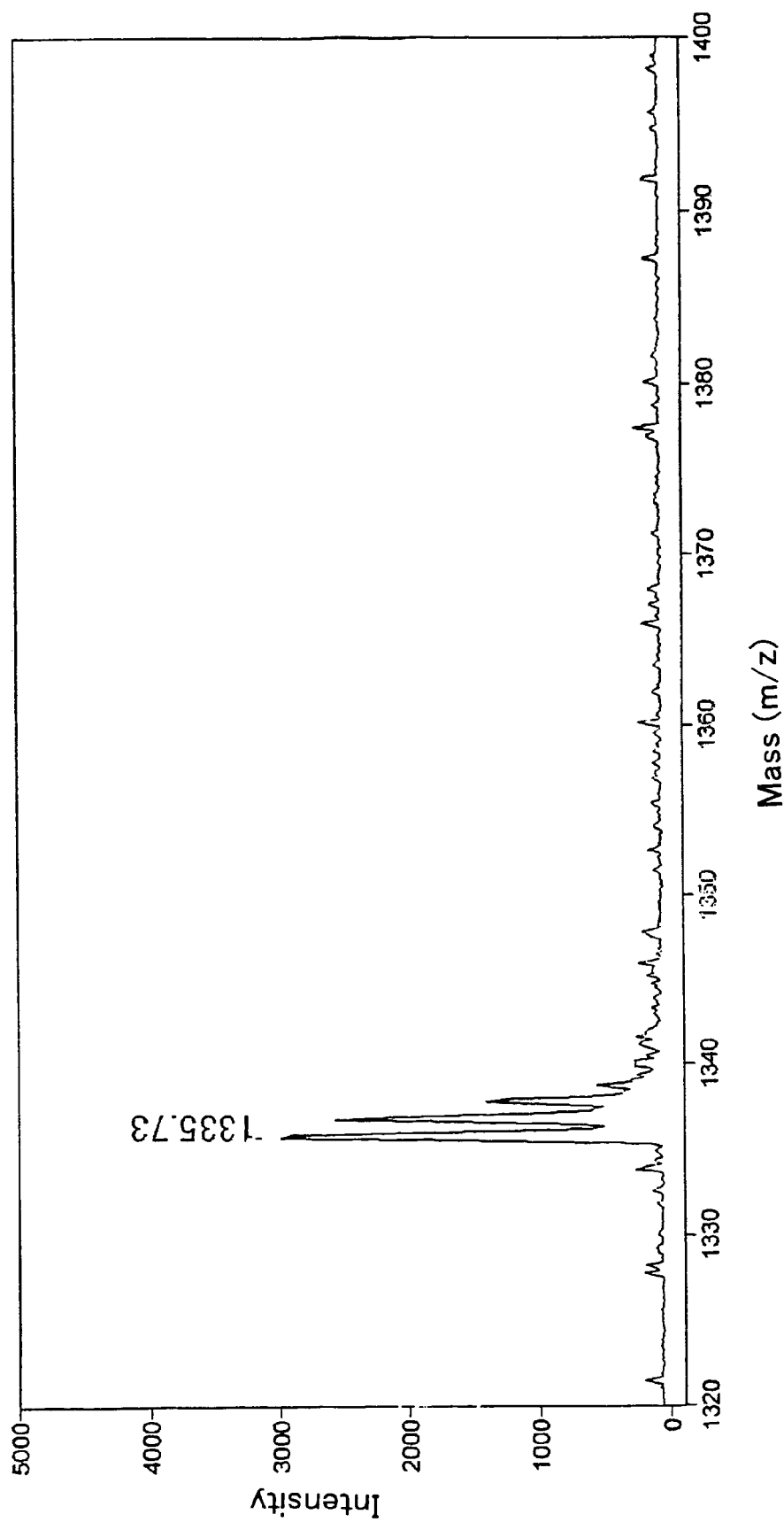
FIG. 7 is a mass spectrum of a composite material of a sample and $^{68}$Zn zinc complex. By comparing FIG. 7 with FIG. 6, a molecular weight of a phosphoric acid monoester compound can be identified.

The results of the mass spectrometry on the composite compounds including $^{64}$Zn zinc isotope and $^{68}$Zn zinc isotope are shown in FIG. 6 and FIG. 7, respectively.

According to the results, it is clearly observed that, as well as Test Example 1, the sample was monophosphate-esterified and the number of the bonded phosphate group was one. In addition, both of the molecular ion peaks appeared in almost identical shapes, and it was found that a molecular weight of a phosphoric acid monoester compound was easily identified even when a mixed sample such as biological sample was used. The value subtracted a molecular weight (581) of the complex compound from a molecular weight of the composite material including $^{64}$Zn zinc was 747. The value is different from that shown in the above structural formula, because it is considered that the phosphoric acid monoester group was ionized as the result of Test Example 1. Therefore, adding a molecular weight of the eliminated hydrogen positive ion gives 749.

INDUSTRIAL APPLICABILITY

The present invention provides a method for confirming existence of a phosphoric acid monoester compound (phosphorylated peptide, and the like) and easily identifying a molecular weight thereof even among biological samples including a plurality of compounds. Thus, the present invention is useful in diagnosing diseases or the like when the present method is applied to biological samples or the like. Further, an additive for mass spectrometry according to the present invention is very useful in an industrial aspect, as it can be used for the present invention.

The invention claimed is:

1. A method for identifying a molecular weight of a phosphoric acid monoester compound, comprising steps of:
   (a) mixing a complex compound including a compound (I) having single kind of zinc isotopes and a sample in a solvent to obtain a solution, and then acquiring a mass spectrum of the solution,

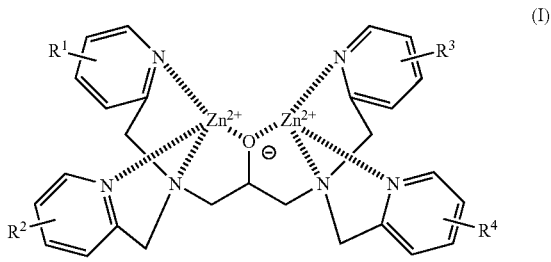

(I)

wherein $R^1$ to $R^4$ are identical to or different from each other, and are hydrogen atoms or substituents selected from a group consisting of a straight chain or a branched chain C1-C6 alkyl group, an amino group, a hydroxy group, a carbamoyl group, a straight chain or a branched chain C1-C6 alkoxy group, a halogen atom, a nitro group, a sulfonic acid group, a carboxyl group, a formyl group, an acyl group, a cyano group, an aminomethyl group, a hydroxymethyl group;
   (b) mixing a complex compound including a compound (I) having another kind of zinc isotopes and the sample in a solvent to obtain a solution, and then acquiring a mass spectrum of the solution; and
   (c) identifying the molecular weight of the phosphoric acid monoester compound by comparing the mass spectra.

2. The method according to claim 1, wherein all of $R^1$ to $R^4$ in the complex compound used for the method are hydrogen atoms.

3. An additive for a mass spectrometry used for identifying a molecular weight of a phosphoric acid monoester compound, comprising:
   a reagent having a complex compound including a compound (I) having a single kind of zinc isotopes, and a reagent having a complex compound including a compound (I) having another kind of zinc isotopes;

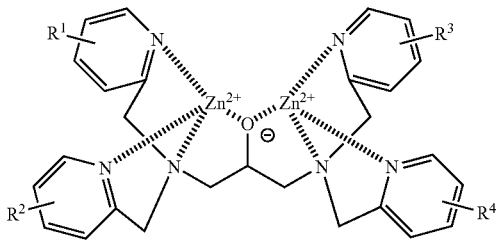

wherein $R^1$ to $R^4$ are identical to or different from each other, and are hydrogen atoms or substituents selected from a group consisting of a straight chain or a branched chain C1-C6 alkyl group, an amino group, a hydroxy group, a carbamoyl group, a straight chain or a branched chain C1-C6 alkoxy group, a halogen atom, a nitro group, a sulfonic acid group, a carboxyl group, a formyl group, an acyl group, a cyano group, an aminomethyl group, a hydroxymethyl group.

4. The additive for a mass spectrometry according to claim 3, wherein all of $R^1$ to $R^4$ of the complex compound in the reagent are hydrogen atoms.

5. The additive for a mass spectrometry according to claim 4, wherein the complex compound further forms a complex of the compound (I) and an acetate ion.

6. The additive for a mass spectrometry according to claim 3, wherein the reagent is in a state of a salt.

7. The additive for a mass spectrometry according to claim 3, wherein the reagent is in a state of a solution.

8. The additive for a mass spectrometry according to claim 3, wherein the complex compound further forms a complex of the compound (I) and an acetate ion.

* * * * *